United States Patent [19]

Fried et al.

[11] 4,323,564
[45] Apr. 6, 1982

[54] ESTERS OF 6-CHLORO-11β, 17α,21-TRIHYDROXYPREGNA-1,4,6-TRIENE-3,20-DIONE

[75] Inventors: John H. Fried, Palo Alto; Denis J. Kertesz, Mountain View; Michael Marx, Sunnyvale, all of Calif.

[73] Assignee: Syntex (U.S.A.) Inc., Palo Alto, Calif.

[21] Appl. No.: 884,933

[22] Filed: Mar. 9, 1978

Related U.S. Application Data

[63] Continuation-in-part of Ser. No. 791,911, Apr. 24, 1977, abandoned.

[51] Int. Cl.³ .......................... A61K 31/58; C07J 5/00
[52] U.S. Cl. .......................... 424/241; 260/239.55 D; 260/397.45; 424/243
[58] Field of Search .................. 260/239.55 D, 397.45

[56] References Cited

U.S. PATENT DOCUMENTS

| | | | |
|---|---|---|---|
| 2,838,499 | 6/1958 | Spero et al. | 260/239.55 |
| 3,232,965 | 2/1966 | Ringold et al. | 260/397.45 |
| 3,312,591 | 4/1967 | Elks et al. | 260/397.45 |
| 3,422,193 | 1/1969 | Shapiro et al. | 260/397.45 |

*Primary Examiner*—Elbert L. Roberts
*Attorney, Agent, or Firm*—Tom M. Moran; Alan M. Krubiner

[57] ABSTRACT

The 17-butyrate, 17-benzoate, 17,21-methyl orthobutyrate, 17,21-methyl orthobenzoate, and 17,21-dibutyrate esters of cloprednol (6-chloro-11β, 17α, 21-trihydroxypregna-1,4,6-triene-3,20-dione) are useful as topical, anti-inflammatory steroids.

8 Claims, No Drawings

ESTERS OF 6-CHLORO-11β, 17α,21-TRIHYDROXYPREGNA-1,4,6-TRIENE-3,20-DIONE

This is a continuation-in-part of U.S. patent application Ser. No. 791,911, filed Apr. 24, 1977, now abandoned.

BACKGROUND OF THE INVENTION

1. Field of the Invention

This invention relates to a new class of steroidal anti-inflammatory compounds. More specifically, it relates to certain 17-esters, a 17,21-diester and 17,21-orthoesters of cloprednol, (6-chloro-11β,17α,21-trihydroxypregna-1,4,6-triene-3,20-dione), and their use as topical anti-inflammatories.

2. Prior Art

Cloprednol and its 21-esters are known compounds as set forth in U.S. Pat. No. 3,232,965 to Ringold and Rosenkranz. The compound and its 21-esters are generally given orally to aid in reducing the pain of arthritis and other inflammatory conditions. It is generally known that certain 17-esters of pregnadienes can be prepared by forming the 17,21-orthoester of the 17,21-diol and hydrolyzing the orthoester to obtain a 17-acetate. See for example, French Pat. No. 1,469,675; U.S. Pat. No. 3,980,778; and German Patent Application DT No. 2,055,221.

It has been suggested in a Report dated Dec. 15, 1975 published by Kidder, Peabody and Co. entitled "The Drug Industry—Hormones: Topical Corticosteroids" that cloprednol might be applied topically and may promise a short-acting steroid molecule that might offer toxicity advantages over older steroids. Unfortunately, cloprednol itself exhibites limited topical, anti-inflammatory activities. Although the 21-esters of cloprednol exhibit slightly greater topical anti-inflammatory activity (as estimated by a vasoconstriction assay) than cloprednol and appear to have short half-lives, as does cloprednol, they exhibit substantial systemic activity as measured in small animal assays. It is desirable, of course, to use topical corticosteroids which have a favorable therapeutic ratio of anti-inflammatory systemic activity, i.e. the higher the value of the ratio, the better the compound, assuming the topical activity is in the correct range. Surprisingly, we have now discovered that certain 17-esters, a 17,21-diester and certain 17,21-orthoesters of cloprednol exhibit a more favorable therapeutic ratio of anti-inflammatory (i.e. vasoconstriction) to systemic activity than cloprednol itself or the corresponding 21-esters and that the compounds of this invention are also unexpectedly superior to the heretofore unknown 17-acetate of cloprednol.

SUMMARY OF THE INVENTION

The primary aspect of this invention is a compound chosen from those represented by the formula

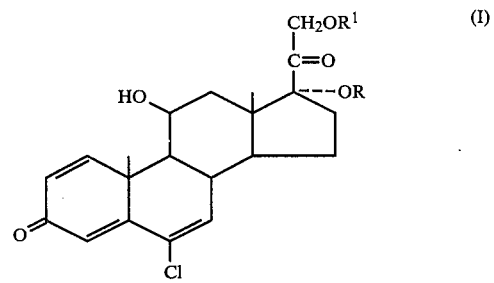

wherein R is butyryl or benzoyl when $R^1$ is hydrogen or R is butyryl when $R^1$ is butyryl, or $R^1$ and R together are represented by

wherein $R^2$ is propyl or phenyl.

Another aspect of this invention is a topical, anti-inflammatory composition which comprises an effective amount of one of the above compounds with a suitable pharmaceutical excipient.

Still another aspect of this invention is a process for treating an inflamed skin condition by contacting the inflamed area with an effective amount of a compound of the invention.

Still another aspect of this invention is a process for preparing a compound of this invention by a process set forth hereafter.

PREFERRED EMBODIMENTS

Preferred compounds encompassed by the scope of this invention include the 17-butyrate; 17-benzoate; and 17,21-methyl orthobutyrate.

ADMINISTRATION AND FORMULATION

The compounds of this invention are useful for the relief of inflammatory manifestations of corticosteroid responsive dermatoses.

Generally, the inflammatory manifestation in mammals, particularly humans, is combatted by contacting the inflamed area with an effective amount of the novel steroids of this invention, that is an amount which results in improvement of the inflamed condition. Preferably the steroids are first formulated to prepare a suitable pharmaceutical formulation, as discussed hereinafter, which is then placed in contact with the afflicted area. An effective amount will depend upon the particular condition and the animal receiving the treatment, but will vary between 0.001% to 10% by weight of the pharmaceutical composition and preferably will be between about 0.01 and 2% by weight of the formulation. Using these levels in the formulation, a therapeutically effective and non-toxic amount, ie. enough to effect an anti-inflammatory response, but not enough to harm the recipient, is applied to the inflamed area.

The compounds of this invention not only have anti-inflammatory activity but also appear to exhibit a low level of systemic activity, as measured by small animal assays. This allows for the application of an effective amount of the anti-inflammatory compounds without an adverse effect on the rest of the animal's system.

The novel steroids of this invention may be formulated with suitable pharmaceutical vehicles known in the art to form particularly effective topical, anti-inflammatory compositions. The rest of the formulated composition will be about 90%w to about 99.999%w, preferably about 98%w to about 99.99%w, of a suitable excipient which may include a pharmaceutically acceptable solvent and other pharmaceutically acceptable additives to form a topically effective pharmaceutical formulation.

A pharmaceutically acceptable solvent is one which is substantially non-toxic and non-irritating under the conditions used and may be readily formulated into any of the classical drug formulations such as creams, ointments, lotions, gels, or the like. Particularly suitable solvents include water, glycerine, propylene carbonate, and a glycol such as b 1,2-propylene diol (i.e. propylene glycol), 1,3-propylene diol, polyethylene glycol having a molecular weight of from 100 to 10,000, dipropylene glycol, etc.; and mixture of the aforementioned with each other.

A topical, anti-inflammatory cream may be prepared as a semi-solid emulsion of oil in water or water in oil. A cream base formulation by definition is an emulsion which is a two phase system with one liquid (for example fats or oils) being dispersed as small globules in another substance (e.g., a glycol-water solvent phase) which may be employed as the primary solvent for the novel steroids of this invention. Other than the solvent with the steroids therein, the cream formulation may contain fatty alcohols, surfactants, mineral oil or petrolatum and other typical pharmaceutical adjuvants such as anti-oxidants, antiseptics, or compatible adjuvants. A typical cream base formulation is given in U.S. Pat. No. 3,934,013 to Poulsen and as much of that patent as is pertinent is incorporation herein by reference.

The novel steroids of this invention may also be formulated as ointments. A "classical" ointment is a semi-solid anhydrous composition which may contain mineral oil, white petrolatum, a suitable solvent such as a glycol and may include propylene carbonate and other pharmaceutically suitable additives such as surfactants, for example Span and Tween or wool fat (lanolin), along with stabilizers such as antioxidants and other adjuvants as mentioned before.

Other suitable ointment base formulations which contain propylene carbonate are described in U.S. Pat. No. 4,017,615 to Shastri et al entitled "Propylene Carbonate Ointment Vehicle" and U.S. Pat. No. 3,924,004 to Chang et al. As much of those patents as is pertinent is incorporated herein by reference.

Suitable solvents, surfactants, stabilizers, etc. are discussed in U.S. Pat. No. 3,934,013 and such discussion is incorporated herein by reference.

A suitable "non-classical" anhydrous, water-washable "ointment type" base is described in U.S. Pat. No. 3,592,930 to Katz and Neiman, and as much of that disclosure as is pertinent is incorporated herein by reference.

The fatty alcohols which are suitable have been previously disclosed above in this specification and in U.S. Pat. No. 3,592,930. As much of that disclosure as is pertinent is incorporated herein by reference.

Process for Making the Compounds of the Invention

The starting compound for the process for preparing the compounds of this invention is, of course, cloprednol. This can be prepared by methods as set forth in U.S. Pat. No. 3,232,965. For example, by following Example 4 of the '965 patent and hydrolyzing the 21-acetate, cloprednol is obtained.

The process for preparing the compounds of this invention comprises reacting cloprednol with trimethyl orthobenzoate or trimethyl orthobutyrate to form the $17\alpha,21$-orthoester; hydrolyzing the thus formed $17\alpha,21$-orthoester to form the $17\alpha$-benzoate or $17\alpha$-butyrate; and reacting the $17\alpha$-butyrate with a butyric anhydride or acid chloride to form the $17\alpha,21$-dibutyrate according to the following reaction sequence:

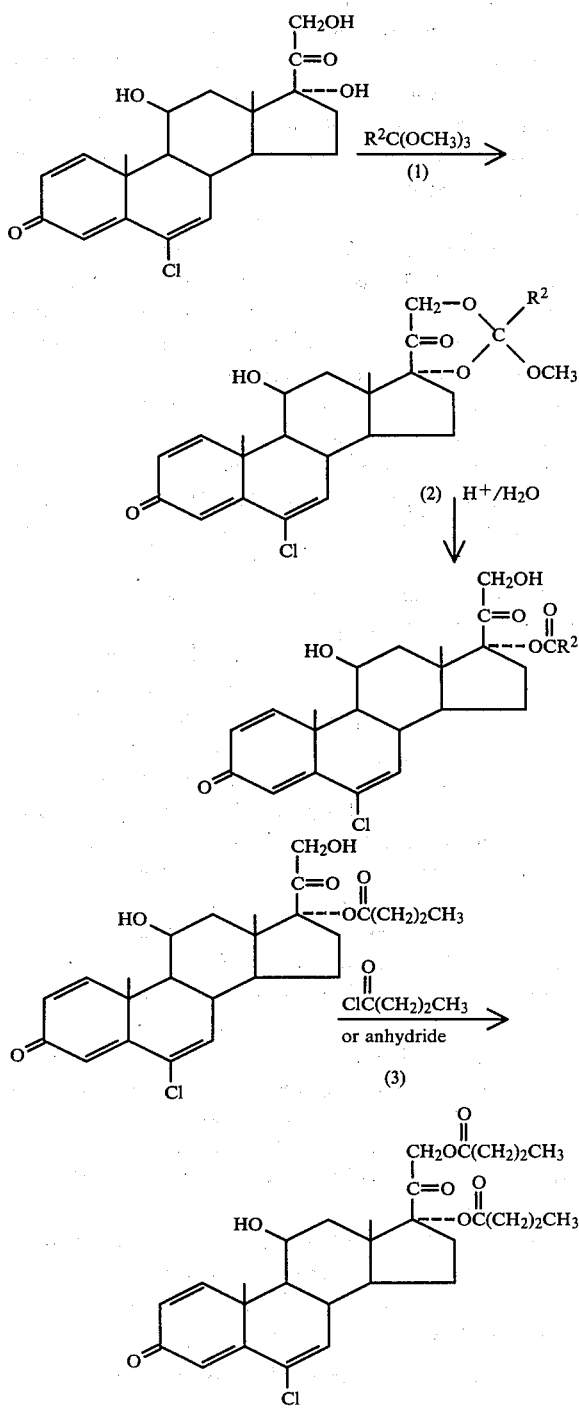

wherein $R^2$ is phenyl or propyl.

(1) The first step in the process for preparing the 17α,21-orthoesters of this invention is performed by mixing a substantial molar excess of the trimethyl orthoester, $R^2C(OCH_3)_3$, with cloprednol in the presence of a catalytic amount of a suitable acid. The reaction can be carried out neat or in the presence of a suitable solvent. If neat, the excess orthoester acts as a diluting agent to aid in reaction and a molar excess of at least 10 moles of the orthoester per mole of cloprednol is used, preferably about 30–40:1. If a solvent is employed a molar excess of less than 10 moles of the orthoester per mole cloprednol is required. Suitable solvents which can be used include inert organic solvents such as benzene, toluene, and the like. Suitable acid catalysts include p-toluenesulfonic acid (pTSA), sulfuric acid, perchloric acid, methanesulfonic acid, and the like. The reaction takes place at temperature of about 50° C. to about 150° C., preferably at about 110° C. to 120° C. neat or at the boiling point of the orthoester solvent, whichever is lower. Generally, the reaction goes to completion in less than 5 hours, 1–2 hours being sufficient for the neat reaction at 110°–120° C. Once the reaction is completed, the 17α,21-orthoester of cloprednol is isolated and purified by using well established means such as extraction, separation, solvent evaporation, recrystallization and thin-layer chromatography (TLC).

(2) Once the 17α,21-orthoester of cloprednol is obtained it is contacted with a buffered aqueous alcohol solution to hydrolyze the 17α,21-orthoester and form the 17α-ester. A suitable buffering agent is potassium hydrogen phosphate buffer having a pH of 3–3.5. Suitable alcohols include methanol, ethanol, propanol and the like. A mixture of 5–10 parts by volume of the alcohol solvent per part of the aqueous buffer has been found to be suitable. The reaction takes place at temperatures of 20° C. to 60° C. At about 25° C. the reaction is complete in 24 hours or less. The 17α-ester is then purified by methods well-known in the art, e.g. extraction, solvent evaporation, crystallization, TLC, etc.

(3) To obtain the 17α,21-butyrate, the 17α-butyrate is reacted with a butyric acid chloride or acid anhydride in a solvent in the presence of an organic base. Bases which may be used include pyridine, 4-dimethylaminopyridine, triethylamine and the like, while suitable solvents are chloroform, methylene chloride, benzene and the like. In a preferred procedure, pyridine is used both as the base and the solvent. The acid chloride or anhydride is present in a substantial molar excess such as 5–20 moles of the acid chloride per mole of 17α-ester. Enough base is used to neutralize the acid formed by the reaction, thus at least one mole of base is needed per mole of 17α-ester. Generally, the reaction takes place readily at temperature of 0°–50° C., preferably at about 20° C.–30° C.

The following specific examples are presented to further illustrate the present invention but are not intended to limit the scope thereof.

EXAMPLE 1

This example sets forth a method for preparing the 17α,21-ortho esters of cloprednol.

A. Three hundred milligrams (mg) of cloprednol is added to a 60 milliliter (ml) flask along with 5 ml of trimethyl orthobutyrate and a 50 mg of dry p-toluenesulfonic acid (pTSA). The mixture is stirred for 1 hour under nitrogen at 120° C. in a water bath until the reaction is complete. Fifty ml of ethyl acetate along with 100 ml of water are added to the reaction mixture. After separating the water from the resulting organic phase, the latter is washed with three, 50 ml portions of water. The resulting organic mixture is dried over sodium sulfate, stripped and vacuum dried to give a yellow oil. The material is placed on a 0.75 millimeter (mm) by 1 meter (m) TLC plate and developed three times with a 3% methanol: 97% chloroform solvent mixture followed by extraction and crystallization from acetone-hexane to ultimately give 185 mg of approximately 95% pure 6-chloro-11β,17α,21-trihydroxypregna-1,4,6-triene-3,20-dione 17,21-methyl orthobutyrate, melting point (mp) 120°–122° C.

B. Similarly, by following the above procedure but substituting trimethyl orthobenzoate for trimethyl orthobutyrate, the following compound is obtained:

6-chloro-11β,17α,21-trihydroxypregna-1,4,6-triene-3,20-dione 17,21-methyl orthobenzoate, mp 144°–148° C. (amorphous foam).

EXAMPLE 2

This example sets forth a method for preparing the 17-esters of cloprednol.

A. One hundred eighty mg of 6-chloro-11β,17α,21-trihydroxypregna-1,4,6-triene-3,20-dione 17,21-methyl orthobutyrate as prepared according to Part A of Example 1, 6 ml of methanol and 1 ml of potassium hydrogen phosphate buffer (pH 3.1) are added to a 50 ml flask. The mixture is stirred overnight (approximately 17 hours) at room temperature which results in about 70% completion of the reaction. An additional 30 ml of methanol and 5 ml of potassium hydrogen phosphate buffer are added and the mixture is heated to 60° C. on a hot water bath for about 1 hour to bring the reaction to completion very cleanly. The reaction mixture is partitioned between ethyl acetate and water and the ethyl acetate is removed by vacuum evaporation to give an oil which is then chromatographed on a 0.75 mm×1 m TLC plate by developing two times with 3% methanol in chloroform to give 130 mg of 6-chloro-11β,17α,21-trihydroxypregna-1,4,6-triene-3,20-dione 17-butyrate, m.p. 115°–120° C. (amorphous form).

B. By following the procedure set forth in Part A but substituting the 17,21-methyl orthobenzoate obtained according to part B of Example 1 for the 17α,21-methyl orthobutyrate, the 17-benzoate is obtained, m.p. 244°–248° C.

EXAMPLE 3

This example sets forth a process for preparing the 17α,21-butyrate of cloprednol.

A. Ninety-nine mg of the 17α-butyrate of cloprednol as prepared in Part A of Example 2 above are placed in a suitable flask along with 3 ml of pyridine and 0.2 ml of butyryl chloride and stirred for 2 hours at room temperature. The reaction mixture is then placed in the refrigerator overnight (about 17 hours) after which the reaction is complete. The reaction mixture is poured into dilute aqueous sodium carbonate and extracted with ethyl acetate. The organic phase is washed another time with dilute aqueous sodium carbonate, then four times with water, dried over sodium sulfate and the solvent is removed by vacuum evaporation. The product is purified by chromatography on a 0.75 mm×1 meter TLC plate developing with 25% acetone/75% hexane to afford 80 mg of 6-chloro-11β,17α,21-trihydroxypregna-1,4,6-triene-3,20-dione 17,21-dibutyrate, m.p. 129°–132° C.

EXAMPLE 4

This example sets forth data comparing the topical activities of the 17α-acetate of cloprednol versus the novel 17-esters, 17,21-dibutyrate and 17,21-orthoesters of this invention. The topical anti-inflammatory activity potential for each compound was assayed using a modified Stoughton/McKenzie vasco-constriction assay in humans, i.e., McKenzie, S. W. and Stoughton, R. B. "Method for Comparing Percutaneous Absorption of Steroids" *Arch. Dermat.* 86, 608 (1962).

Eight normal adult human subjects were treated on each forearm by topical administration with alcoholic solutions containing $1\times10^{-4}$ and $1\times10^{-5}$ g/ml of each of the compounds to provide 64 total test sites for each compound in a series (32 for each concentration). Areas of the subjects' forearms were outlined by a rubber stamp grid coated with silicone grease, and 10 lambda are applied per 7×7 mm. square site. After the preparations have dried, the areas on each forearm are covered with Saran ® wrap and the margins sealed with tape. The occlusive wrap is removed after 18 hours. Twenty-four hours after application, the presence of vasoconstriction is noted by visual examination, and expressed as the number of sites responding (vasoconstriction). The number of sites responding by vasoconstriction is also calculated as a percentage of the total number of sites. Cloprednol 17-acetate is used as a standard, its activity being indicated as 1.

TABLE I

| No. | Cloprednol Esters | Vasoconstrictive Activity |
|---|---|---|
| 1 | 17-acetate | 1 |
| 2 | 17-butyrate | 8 |
| 3 | 17-benzoate | 7 |
| 4 | 17,21-dibutyrate | 3 |
| 5 | 17,21-methyl orthobutyrate | 7 |
| 6 | 17,21-methyl orthobenzoate | 3 |

The subject matter claimed is:

1. A compound chosen from those represented by the formula (I)

wherein
R is butyryl or benzoyl when $R^1$ is hydrogen, or R is butyryl when $R^1$ is butyryl, or
R and $R^1$ taken together are represented by (II)

wherein
$R^2$ is propyl or phenyl.

2. The compound of claim 1 wherein $R^1$ is hydrogen and R is butyryl, 6-chloro-11β,17α,21-trihydroxypregna-1,4,6-triene-3,20-dione 17-butyrate.

3. The compound of claim 1 wherein $R^1$ is hydrogen and R is benzoyl, 6-chloro-11β,17α,21-trihydroxypregna-1,4,6-triene-3,20-dione 17-benzoate.

4. The compound of claim 1 wherein R and $R^1$ are both butyryl, 6-chloro-11β,17α,21-trihydroxypregna-1,4,6-triene-3,20-dione 17,21-dibutyrate.

5. The compound of claim 1 wherein R and $R^1$ together are and $R^2$ is phenyl, 6-chloro-11β,17α,21-trihydroxypregna-1,4,6-triene-3,20-dione 17,21-methyl orthobenzoate.

6. The compound of claim 1 wherein R and $R^1$ together are and $R^2$ is propyl, 6-chloro-11β,17α,21-trihydroxypregna-1,4,6-triene-3,20-dione 17,21-methyl orthobutyrate.

7. A topical, pharmaceutical, anti-inflammatory composition which comprises a pharmaceutically acceptable excipient in combination with an effective amount of a compound of claim 1.

8. A method of relieving a topical inflammatory condition in mammals which comprises contacting the afflicted area with an effective amount of a compound of claim 1.

* * * * *